United States Patent [19]

Coll-Palagos et al.

[11] 4,309,409

[45] Jan. 5, 1982

[54] ANTI-CORROSION FORMULATION FOR TOOTHPASTES

[75] Inventors: Miguel Coll-Palagos, Rye; Frances C. Benkwitt, Yonkers, both of N.Y.

[73] Assignee: Stauffer Chemical Company, Westport, Conn.

[21] Appl. No.: 120,012

[22] Filed: Feb. 8, 1980

Related U.S. Application Data

[63] Continuation of Ser. No. 733,734, Oct. 26, 1976, abandoned, and a continuation-in-part of Ser. No. 643,444, Dec. 22, 1975, abandoned.

[51] Int. Cl.$^3$ ............................................. A61K 7/16
[52] U.S. Cl. ........................................ 424/52; 424/57
[58] Field of Search ..................................... 424/49–58

[56] References Cited

U.S. PATENT DOCUMENTS

| | | | |
|---|---|---|---|
| 2,018,410 | 10/1935 | McDonald et al. | 424/49 |
| 2,078,498 | 4/1937 | Klarmann et al. | 424/49 |
| 3,095,356 | 6/1963 | Clayton | 424/49 |
| 3,227,617 | 1/1966 | Manahan et al. | 424/52 |
| 3,227,618 | 1/1966 | Manahan | 424/52 |
| 3,282,792 | 11/1966 | Fiscella | 424/52 |
| 3,357,790 | 12/1967 | Saunders | 424/49 |
| 3,622,662 | 11/1971 | Roberts et al. | 424/49 |
| 3,624,199 | 11/1971 | Norfleet | 424/49 |
| 3,662,060 | 5/1972 | Clippingdale | 424/49 |
| 3,678,155 | 7/1972 | Clippingdale | 424/49 |

*Primary Examiner*—Shep K. Rose
*Attorney, Agent, or Firm*—Richard P. Fennelly

[57] ABSTRACT

A formulation which consists essentially of from about 20%, by weight, to about 87%, by weight, zinc oxide, from about 13% to about 80%, by weight of a selected type of acidic pH adjuster, and from about 0% to about 7%, by weight, of trimagnesium phosphate, when incorporated in fluorine-containing toothpaste formulations which also contain at least one compound selected from the group consisting of an insoluble alkali metal metaphosphate and calcium pyrophosphate, yields a smooth paste having a pH of from about 5.5 to about 6.8 which will not corrode the inside of unlined aluminum tubes containing such a formulation. When the components of the formulation are based on the weight of the entire toothpaste formulation, said zinc oxide can be present at from about 0.05% to about 2.0%, the acidic pH adjuster can be present at from about 0.05% to about 3.0%, and the trimagnesium phosphate can be present at from about 0% to about 0.5%.

18 Claims, No Drawings

ANTI-CORROSION FORMULATION FOR TOOTHPASTES

RELATED APPLICATION

This is a continuation, of application Ser. No. 733,734 filed Oct. 26, 1976 now abandoned and a continuation-in-part application of copending U.S. Ser. No. 643,444, filed Dec. 22, 1975 now abandoned.

TECHNICAL DESCRIPTION OF THE INVENTION

The present invention is a formulation, which when incorporated in toothpastes containing a fluorine containing compound and at least one compound selected from the group consisting of an insoluble alkali metal metaphosphate and calcium pyrophosphate that are held in unlined aluminum tubes, gives a paste which has acceptable pH values for efficacy of said flourine containing compound, acceptable texture, and a noncorrosive effect on the inside of the unlined aluminum tube in which it is held.

It has been recognized that toothpaste formulations which contain a polishing material which includes a major amount of an insoluble alkali metal metaphosphate cannot be placed in unlined aluminum tubes without corrosion problems being caused. One prior art attempt to overcome this problem is described in U.S. Pat. No. 3,624,199 to J. Norfleet et al. which suggests using 0.5 to 5%, by weight, benzyl alcohol and 0.15 to 2%, by weight, zinc oxide in such toothpaste formulations. The zinc oxide is identified as being responsible for prevention of corrosion of the unlined aluminum tube containing such a toothpaste formulation, whereas the benzyl alcohol is merely identified as a desensitizing agent for tender areas and membranes in the oral cavity.

Although the use of zinc oxide alone in a toothpaste, wherein a desensitizing agent is not needed, will inhibit the corrosion of unlined aluminum tubes, it has been found that the desired pH values have been exceeded for efficacy of the fluoride compounds that may be contained therein.

It has been found that this problem can be solved by combining the zinc oxide with an effective amount of a selected type of acidic pH adjuster to both lower the pH of the paste to the desired range of from about 5.5 to 6.8, preferably 5.5–6.5, and to prevent hindrance of the anti-corrosion effect of the zinc oxide on the tube. Additional improvements in paste texture can be obtained by incorporating in the formulation an effective amount for such improvement of trimagnesium phosphate.

The formulation of the present invention contains zinc oxide, an acidic pH adjuster, which will be described in greater detail below, and, optionally, trimagnesium phosphate. These components can be preblended to form such a formulation or can be added individually to a dental cream when the other solid constituents are added. In either case, the amount of zinc oxide which is used must be effective to inhibit any appreciable corrosion of the unlined aluminum tube, the amount of the selected acidic pH adjuster must be effective to both maintain a pH in the toothpaste which is acceptable for any fluoride compound which is present therein and to not hinder the anti-corrosive action of the zinc oxide, and the amount of trimagnesium phosphate, if such is used, must be effective to bring about any desired improvement in texture. Generally the anti-corrosion formulation itself should consist essentially of from about 20% to about 87% by weight, zinc oxide, from about 13% to about 80% by weight of the acidic pH adjuster and from about 0% to about 7% by weight of trimagnesium phosphate. Preferred amounts are about 40-67% zinc oxide, about 33%-60% pH adjuster and about 0%-5% trimagnesium phosphate.

The amount of the above preblended formulation, or individual components thereof, which is added to the toothpaste must, as described above, be sufficient to give acceptable pH values and texture and prevent corrosion of the unlined aluminum tube. Generally, the final content of zinc oxide in the paste containing the above-described components will be from about 0.05% to about 2.0%, preferably from about 0.1 to about 1.5%, the amount of acidic pH adjuster will be from about 0.05% to about 3.0%, preferably from about 0.2% to about 1.5%, and the amount of trimagnesium phosphate will be from about 0 to about 0.5%, preferably from about 0.07% to about 0.2%, by weight.

The acidic pH adjuster is selected from the group consisting of weak organic or inorganic acids, and the salts thereof which will form relatively insoluble aluminum compounds with the aluminum tube which contains the toothpaste. Phosphoric acid and its acid salts (sodium aluminum phosphate [1:3:8], magnesium dihydrogen phosphate, aluminum dihydrogen phosphate, and ammonium dihydrogen phosphate) give the best long term results. Other acidic pH adjusters which can be used include boric acid, oxalic acid and tartaric acid.

The above-described anti-corrosion formulation is adapted to be used in a fluorine toothpaste containing at least one compound selected from the group consisting of an insoluble alkali metal metaphosphate and calcium pyrophosphate. The toothpaste formulations of this type are well known and contain a number of ingredients which will now be described in greater detail:

Polishing Agent: The water-insoluble polishing material of the toothpaste formulation of interest herein contains a major proportion (that is, from about 50 percent to 100 percent, by weight, of the polishing material) of an insoluble alkali metal metaphosphate or calcium pyrophosphate. The insoluble alkali metal metaphosphates which may be used are preferably the insoluble sodium and potassium salts of polymetaphosphoric acid. These materials are known in the art with the insoluble sodium metaphosphate being preferred. Such materials may be formed in any suitable manner, as illustrated by Thorpe's Dictionary of Applied Chemistry, Vol. 9 (4th ed.) pp. 510–511. The forms of insoluble sodium metaphosphate known as Madrell's salt and Kurrol's salt are further examples of suitable materials. These metaphosphate salts exhibit only limited solubility in water, and are commonly referred to as insoluble metaphosphates. There is commonly present a minor amount of soluble phosphate material as impurities, usually of the order of a few percent such as up to about 4% by weight. The insoluble alkali metal metaphosphate is typically employed in powder form of a size such that no more than about 1% of the material is larger than about 44 microns.

The polishing material may contain 100% of the insoluble alkali metal metaphosphate or calcium pyrophosphate or any of these agents in major amount in admixture with a minor amount of such other agents or polishing agents as dicalcium phosphate, tricalcium phosphate, calcium pyrophosphate, hydrated alumina, calcium carbonate, and the like.

The polishing material content of the dental cream can be varied, but will generally be from about 20 to about 75% by weight of the total composition.

Liquid Ingredients: In the dental cream formulation, liquids and solids are proportioned to form a creamy mass of desired consistency. In accordance with this invention, the creamy mass is packaged in a collapsible unlined aluminum tube.

In general, the liquids in the dental cream will comprise chiefly water, glycerine, aqueous solutions of sorbitol, propylene glycol, polyethylene glycol 400 and the like, including suitable mixtures thereof. It is advantageous to sometimes use a mixture of both water and a humectant, such as glycerine or sorbitol. The total liquid content will generally be from about 20 to about 75% by weight of the formulation. It is preferred to also use a binder or gelling agent in dental creams such as the natural and synthetic gums and gumlike materials, e.g., Irish moss, gum tragacanth, sodium carboxymethyl cellulose, polyvinylpyrrolidone, and the like, usually in an amount up to about 10%, by weight, and preferably from about 0.2 to about 5%, by weight, of the formulation.

Surface Active Agents: Organic surface-active agents used in the toothpaste formuations of interest herein can be used to assist in achieving through and complete dispersion of the instant compositions and to make them more cosmetically acceptable. The organic surface active material may be anionic, nonionic, ampholytic, or cationic in nature, and it is preferred to employ as the surface active agent a detersive material which imparts to the composition detersive and foaming properties. Suitable materials are the water-soluble salts of higher fatty acid monoglyceride monosulfates, such as the sodium salt of the monsulfated monoglyceride of hydrogenated coconut oil fatty acids, the higher alkyl sulfates, such as sodium lauryl sulfate, the alkyl arylsulfonates, such as sodium dodecyl benzene sulfonate, the higher alkyl sulfoacetates, the higher fatty acid ester of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last-mentioned amides are N-lauroyl sarcosine, and the sodium, potassium, and ethanolamine salts of N-lauroyl, N-myristoyl or N-palmitoyl sarcosinates, which should be substantially free from soap or similar higher fatty acid material which tends to substantially reduce the effect of these compounds.

It is preferred to use from about 0.05 to 5% by weight of the foregoing surface-active materials in the instant dental cream.

Fluoride Compounds: The toothpaste compositions of interest herein also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2KF$), sodium hexafluorozirconate, and sodium monfluorophosphate, which is preferred. These materials, which dissociate or release fluorine-containing ions in water, suitably may be present in an effective but nontoxic amount, usually within the range of about 0.01 to 1% by weight of the water soluble fluorine content thereof. It is necessary that the pH of the formulation be between about 5.5 and 6.8 when these compounds are used.

Flavoring Agents: Any suitable flavoring or sweetening sialagogue may be employed in formulating the dental cream of the instant invention. Examples of suitable examples of flavoring consituents include flavoring oils such as the oils of spearmint, peppermint, clove, wintergreen, sassafras, sage, eucalyptus, marjoram, cinnamon, lemon and orange, as well as sodium salicylate. Suitable sweetening agents include lactose, maltose, sorbitol, and saccharine. Suitably, the total amount of sialagogue may comprise from about 0.5 to about 6% or more of the dental cream of the instant invention.

Other ingredients: Various other materials may be incorporated in the dental creams of this invention. Examples thereof are coloring or whitening agents, preservatives (e.g., sodium benzoate and the esters of the hydroxybenzoates, which are usually considered necessary from a commercial standpoint), silicones and other constituents such as desensitizing agents. These adjuvants can be incorporated in the instant compositions in conventional amounts and will not substantially adversely affect the properties and characteristics of the formulation formed thereby.

The following Examples illustrate certain preferred embodiments of the present invention.

EXAMPLE 1

This Example illustrates the formation of a toothpaste formulation containing the stabilizer formulation of the present invention.

A general procedure for forming the toothpaste includes the following steps:

1. Weigh the desired amounts of thickener, sweetening agent, preservative and sodium monofluorophosphate and premix said ingredients with a spatula;

2. Place a beaker on a ringstand and a mixer in said beaker. Add sorbitol and glycerine and mix them until they are uniform. The ingredients from Step 1 are then added slowly and are mixed. Water is added and mixing is continued; and 3. The beaker containing the mixture from step 2 is weighed and water is added if needed to bring the mixture to the requisite weight. The insoluble sodium metaphosphate is then added and anhydrous dicalcium phosphate, zinc oxide, boric acid, and trimagnesium phosphate are added and are mixed into the formulation with a spatula until a uniform consistency is noted. Detergent and flavor can then be mixed in until a uniform paste is obtained. The mixture is milled into a stainless steel beaker and the batch is deaerated. It is then transferred to filling equipment and is inserted into an unlined aluminum tube.

The above procedure was used to make the following formulation:

| Ingredient(s) | % (by weight) |
| --- | --- |
| Insoluble sodium metaphosphate | 40.25 |
| Water | 19.39 |
| Sorbitol (70% by weight) | 14.00 |
| Glycerine (95% by weight) | 12.80 |
| Anhydrous dicalcium phosphate | 5.00 |
| Misc. agents (Binder, Flavoring, Preservative, etc.) | 4.20 |
| Sodium N-lauroyl sarcosinate detergent | 2.00 |
| Zinc Oxide | 1.00 |
| Sodium monofluorophosphate | 0.76 |
| Boric acid | 0.50 |

-continued

| Ingredient(s) | % (by weight) |
|---|---|
| Trimagnesium Phosphate | 0.10 |

The formulation had a pH in the range of about 5.5 to 6.5 and had a smooth texture. When placed in an unlined aluminum tube for one week's storage at 50° C., the formulation caused no appreciable corrosion of said tube.

EXAMPLE 2

The general procedure used in Example 1 was utilized to form toothpaste formulations containing the following components:

| | (% by weight) | |
|---|---|---|
| Ingredients | A | B |
| Insoluble sodium metaphosphate | 41.85 | 40.25 |
| Anhydrous dicalcium phosphate | 5.00 | 5.00 |
| Sodium monofluorophosphate | 0.76 | 0.76 |
| Sodium N-lauroyl sarcosinate | 2.00 | 2.00 |
| Glycerine | 12.80 | 12.80 |
| Sorbitol | 14.00 | 14.00 |
| Misc. agents (binder, flavoring, preservative) | 4.20 | 4.20 |
| Water | 19.39 | 19.39 |
| Zinc oxide | — | 1.00 |
| Boric acid | — | 0.50 |
| Trimagnesium phosphate | — | 0.10 |

Formulation A, set forth above, corroded unlined aluminum tubes when placed therein whereas formulation B did not.

EXAMPLE 3

This example illustrates both corrosive (formulation A, below) as well as non-corrosive (formulation B, below) formulations using calcium pyrophosphate as the polishing agent. The same general mixing procedure of Example 1 was used and both formulations were placed in unlined aluminum tubes. The following ingredients were used:

| | (% by weight) | |
|---|---|---|
| Ingredients | A | B |
| Calcium pyrophosphate | 45.00 | 43.40 |
| Glycerine (95%) | 4.00 | 4.00 |
| Sodium carboxymethyl cellulose (medium viscosity) | 1.20 | 1.20 |
| Saccharin | 0.20 | 0.20 |
| Sodium benzoate, U.S.P. | 0.10 | 0.10 |
| Sorbitol (70%) | 18.00 | 18.00 |
| Distilled water | 23.00 | 23.00 |
| Flavoring | 1.00 | 1.00 |
| Sodium lauryl sulfate (20%) in glycerine (80%) | 7.50 | 7.50 |
| Zinc oxide | — | 1.00 |
| Boric acid | — | 0.50 |
| Trimagnesium phosphate | — | 0.10 |

EXAMPLE 4

This Example illustrates the effect of removing one or more of the components of the anti-corrosion formulation of the present invention. The table sets forth the various formulations (A-D) which are prepared:

| | (% by weight) | | | | |
|---|---|---|---|---|---|
| Ingredient | A | B | C | D | E |
| Insoluble sodium metaphosphate | 41.85 | 40.85 | 40.35 | 40.25 | 39.75 |
| Anhydrous dicalcium phosphate | 5.00 | 5.00 | 5.00 | 5.00 | 5.00 |
| Glycerine | 12.80 | 12.80 | 12.80 | 12.80 | 12.80 |
| Sorbitol | 14.00 | 14.00 | 14.00 | 14.00 | 14.00 |
| Sodium N-lauroyl sarcosinate | 2.00 | 2.00 | 2.00 | 2.00 | 2.00 |
| Sodium monofluorophosphate | 0.76 | 0.76 | 0.76 | 0.76 | 0.76 |
| Water | 19.39 | 19.39 | 19.39 | 19.39 | 19.39 |
| Binder, preservatives, flavoring, etc. | 4.20 | 4.20 | 4.20 | 4.20 | 4.20 |
| Zinc oxide | — | 1.00 | 1.00 | 1.00 | 1.00 |
| Boric acid | — | — | 0.50 | 0.50 | — |
| Trimagnesium phosphate | — | — | — | 0.10 | 0.10 |
| Sodium aluminum phosphate (138) | — | — | — | — | 1.00 |

Each of the toothpaste formulations set forth in the table were placed in resin coated aluminum tubes and unlined aluminum tubes, respectively. The paste pH and texture were noted. The tubes were examined after they had been stored for 7 days at 50° C. The following results were obtained:

| Formulation | Paste pH | Texture | Tube |
|---|---|---|---|
| A | 5.5–6.5 | Acceptable | Coated - Not corroded |
| A | 5.5–6.5 | Bubbly | Unlined - Corroded |
| B | 7.5–9.0 | Acceptable | Coated - Not corroded |
| B | 7.5–9.0 | Acceptable | Unlined - Not corroded |
| C | 5.5–6.5 | Acceptable | Coated - Not corroded |
| C | 5.5–6.5 | Acceptable | Unlined - Not corroded |
| D | 5.5–6.5 | Acceptable | Coated - Not corroded |
| D | 5.5–6.5 | Acceptable | Unlined - Not corroded |
| E | 5.5–6.5 | Acceptable | Coated - Not corroded |
| E | 5.5–6.5 | Acceptable | Unlined - Not corroded |

Formulation A which did not contain any of the components of the claimed invention yielded a paste having an unacceptable, bubbly texture and produced corrosion in the unlined aluminum tube. Formulation B containing only zinc oxide avoided the problem of corrosion but gave a paste having a pH which is too high for the effectiveness of the fluorine compound contained in the toothpaste. Formulation D, containing trimagnesium phosphate, produced a slightly smoother, and more acceptable, paste texture than Formulation C, which was acceptable.

EXAMPLE 5

This Example illustrates the importance of utilizing, as acidic pH adjusters, compounds which forms insoluble compounds with aluminum. The formulation described in Example 1 was used during the tests. The Table sets forth the results:

| Compound | ZnO/Cpd Weight Ratio | Amount of Corrosion and Other Observations |
|---|---|---|
| Sodium aluminum phosphate (1:3:8)[1] | 1/1 | No corrosion. |
| Monomagnesium phosphate[2] | 1/0.8 | No corrosion. |
| Monoaluminum phosphate[3] | 1/0.75 | No corrosion. |
| Monoammonium phosphate[4] | 1/1 | No corrosion. |
| Sodium acid pyrophosphate | 1/1 | Corrosion present. |
| Boric acid[5] | 1/0.5 | No corrosion. |
| Oxalic acid | 1/0.6 | No corrosion. |
| Phosphoric acid[6] | 1/1.2 | No corrosion. |
| Tartaric acid[7] | 1/1 | No corrosion. |
| Citric acid | 1/1.5 | Corrosion present. |

-continued

| Compound | ZnO/Cpd Weight Ratio | Amount of Corrosion and Other Observations |
|---|---|---|
| Acetic acid | 1/0.4 | Corrosion present. |

Footnotes:
[1]This adjuster is acceptably effective at a level of about 0.25 to about 1.5% by weight of the stabilizer formulation of zinc oxide/pH adjuster/(optionally) trimagnesium phosphate. A suitable product of this type is available under the trademark LEVAIR® from Stauffer Chemical Company, Specialty Chemical Division, Westport, Connecticut. Some slight development of a grainy texture was observed in some pastes containing this adjuster.
[2]Also called magnesium dihydrogen phosphate. Its formula is $Mg(H_2PO_4)_2$.
[3]Also called aluminum dihydrogen phosphate. Its formula is $Al(H_2PO_4)_3$.
[4]Also called ammonium dihydrogen phosphate. Its formula is $NH_4H_2PO_4$.
[5]The pH values of pastes containing this additive tended to drift upward with time and during a one to eight month storage often was above the desired value.
[6]Some off-color and slight thickening of the paste was noted after one week storage at 50° C. when used with relatively low levels of zinc oxide, e.g., 0.5% Zn/0.25% $H_3PO_4$. A 0.8% ZnO/0.5% $H_3PO_4$ mixture kept the paste pH at 6.2 for twenty one months storage at room temperature without corrosion, off-color, or thickening.
[7]Paste aged at 50° C. for one month containing this additive showed significant thickening, whereas at room temperature the thickening was much less.

The salts and acids listed on the foregoing Table which produce corrosion in the unlined aluminum tube are those which do not form relatively insoluble aluminum compounds with the aluminum tube material in which the toothpaste formulation is packaged.

It has been found that when relatively high values of zinc oxide are used relative to the acidic pH adjuster, it is possible for the pH of the toothpaste formulation to drift upwardly upon prolonged storage due to the dynamic nature of the system. For example use of a 2:1 weight ratio of zinc oxide to boric acid (1%:0.5% by weight of the toothpaste formulation) gave a paste pH after one month's storage of 6.5 and after six months storage of 7.3. This can generally be overcome by using a lower relative amount of zinc oxide or a higher relative amount of the acidic pH adjuster. For example, equal weight amounts of zinc oxide and boric acid (0.8%:0.8% by weight based on the weight of the toothpaste) produced a pH of 6.3 after six months storage. It is well within the ability of a person of ordinary skill in the art to adjust the zinc oxide: pH adjuster ratio so as to obtain the desired pH values after desired storage times.

The foregoing is illustrative of certain preferred embodiments of the claimed invention and is not to be construed in a limiting sense. The scope of protection that is sought is set forth in the claims which follow.

What is claimed:

1. A formulation which is adapted to be contained in a fluoride toothpaste containing an effective amount of water soluble fluoride compound for protection from tooth decay and at least one compound selected from the group consisting of an insoluble alkali metal metaphosphate and calcium pyrophosphate, said formulation being adapted to be packaged in an unlined aluminum tube, the formulation consisting essentially of:
   (a) zinc oxide; and
   (b) an acidic pH adjuster selected from the group consisting of phosphoric acid and its acid salts, sodium aluminum phosphate (1:3:8), magnesium dihydrogen phosphate, monomagnesium phosphate, aluminum dihydrogen phosphate, monoaluminum phosphate, ammonium dihydrogen phosphate, monoammonium phosphate, boric aicd, oxalic acid, and tartaric acid; the amounts of (a) and (b) being effective to prevent corrosion of said tube, to maintain the pH of the toothpaste in the range of from about 5.5 to 6.8 and to give a smooth texture to the toothpaste formulation, said formulation being substantially free of sodium acid pyrophosphate, citric acid, or acetic acid as the acidic pH adjuster.

2. A formulation as claimed in claim 1 wherein the zinc oxide is present at from about 20% to about 87% by weight of the formulation.

3. A formulation as claimed in claim 1 wherein the acidic pH adjuster is present at from about 13% to about 80% by weight of the formulation.

4. A formulation as claimed in claim 1 which further comprises trimagnesium phosphate in an amount of up to about 7% by weight of the formulation.

5. A formulation as claimed in claim 1 wherein the zinc oxide is present at from about 40% to about 67% and the acid adjuster is present at about 33% to about 60%.

6. A formulation as claimed in claim 5 wherein trimagnesium phosphate is also present at up to about 5%.

7. A fluoride toothpaste formulation containing an effective amount of a water soluble fluoride compound for protection from tooth decay and at least one compound selected from the group consisting of an insoluble alkali metal metaphosphate and calcium pyrophosphate which is adapted to be packaged in an unlined aluminum tube, said formulation also comprising:
   (a) zinc oxide; and
   (b) an acidic pH adjuster selected from the group consisting of phosphoric acid and its acid salts, sodium aluminum phosphate (1:3:8), magnesium dihydrogen phosphate, monomagnesium phosphate, aluminum dihydrogen phosphate, monoaluminum phosphate, ammonium dihydrogen phosphate, monoammonium phosphate, boric acid, oxalic acid, and tartaric acid;
the amounts of (a) and (b) being effective to prevent corrosion of said tube, to maintain the pH of the toothpaste in the range of from about 5.5 to about 6.8 and to give a smooth texture to the toothpaste, said formulation being substantially free of sodium acid pyrophosphate, citric acid, or acetic acid as the acidic pH adjuster.

8. A formulation as claimed in claim 7 wherein the zinc oxide is present at from about 0.05% to about 2.0% by weight of the formulation.

9. A formulation as claimed in claim 7 wherein the acidic pH adjuster is present at from about 0.05% to about 3.0% by weight of the formulation.

10. A formulation as claimed in claim 7 wherein the trimagnesium phosphate is also present up to about 0.5% by weight of the formulation.

11. A formulation as claimed in claim 7 wherein the zinc oxide is present at about 0.5% to about 1.5% and the acid adjuster is present at about 0.2% to about 1.5%.

12. A formulation as claimed in claim 11 wherein trimagnesium phosphate is also present at up to about 0.2%.

13. A packaged fluoride toothpaste formulation in an unlined aluminum tube, said toothpaste formulation containing an effective amount of a water soluble fluoride compound for protection from tooth decay and at least one compound selected from the group consisting of an insoluble alkali metal metaphosphate and calcium pyrophosphate, said toothpaste formulation also comprising:
   (a) zinc oxide; and
   (b) an acid pH adjuster selected from the group consisting of phosphoric acid and its acid salts, sodium aluminum phosphate (1:3:8), magnesium dihydrogen phosphate, monomagnesium phosphate, aluminum dihydrogen phosphate, monoaluminum phosphate, ammonium dihydrogen phosphate, monoammonium phosphate, boric acid, oxalic acid, and tartaric acid;

the amounts of (a) and (b) being effective to prevent corrosion of said tube, to maintain the pH of the toothpaste in the range of from about 5.5 to about 6.8 and to give a smooth texture to the toothpaste, said formulation being substantially free of sodium acid pyrophosphate, citric acid, or acetic acid as the acidic pH adjuster 14. A formulation as claimed in claim 13 wherein the zinc oxide is present at from about 0.05% to about 2.0%, by weight of the toothpaste formulation.

15. A formulation as claimed in claim 13 wherein the acidic pH adjuster is present at from about 0.05% to about 3.0%, by weight of the formulation.

16. A formulation as claimed in claim 13 wherein the trimagnesium phosphate is also present up to about 0.5%, by weight of the formulation.

17. A formulation as claimed in claim 13 wherein the zinc oxide is present at about 0.5% to about 1.5% and the acid adjuster is present at about 0.2% to about 1.5%.

18. A formulation as claimed in claim 18 wherein trimagnesium phosphate is also present at up to about 0.2%.

* * * * *

UNITED STATES PATENT AND TRADEMARK OFFICE
CERTIFICATE OF CORRECTION

PATENT NO. : 4,309,409
DATED : January 5, 1982
INVENTOR(S) : Miguel Coll-Palagos et al.

It is certified that error appears in the above—identified patent and that said Letters Patent is hereby corrected as shown below:

Col. 7, line 50, -- a -- should appear before "water soluble"; and

Col. 7, line 63, "aicd" should be -- acid --.

Signed and Sealed this

Twenty-seventh Day of July 1982

[SEAL]

Attest:

*Attesting Officer*

GERALD J. MOSSINGHOFF
*Commissioner of Patents and Trademarks*